(12) United States Patent
Wahren et al.

(10) Patent No.: US 6,610,649 B2
(45) Date of Patent: Aug. 26, 2003

(54) INSULIN C-PEPTIDES

(75) Inventors: John Wahren, Djursholm (SE); Bo-Lennart Johansson, Uttran (SE); Hans Jörnvall, Stockholm (SE)

(73) Assignee: Creative Peptides Sweden AB (SE)

( * ) Notice: Subject to any disclaimer, the term of this patent is extended or adjusted under 35 U.S.C. 154(b) by 0 days.

(21) Appl. No.: 09/269,439

(22) PCT Filed: Sep. 26, 1997

(86) PCT No.: PCT/GB97/02627

§ 371 (c)(1), (2), (4) Date: Jul. 8, 1999

(87) PCT Pub. No.: WO98/13384

PCT Pub. Date: Apr. 2, 1998

(65) Prior Publication Data

US 2002/0107175 A1 Aug. 8, 2002

(30) Foreign Application Priority Data

Sep. 27, 1996 (SE) .............................................. 9603533

(51) Int. Cl.⁷ ........................ A61K 38/16; A61K 38/10; A61K 38/08

(52) U.S. Cl. .............................. 514/2; 514/12; 514/16; 514/17; 514/18; 530/324; 530/328; 530/329; 530/330

(58) Field of Search .......................... 514/1, 12, 16–18; 530/324, 328, 329, 330

(56) References Cited

U.S. PATENT DOCUMENTS

| | | | | |
|---|---|---|---|---|
| 3,953,418 A | | 4/1976 | Yanaihara et al. ....... | 260/112.7 |
| 5,104,854 A | | 4/1992 | Schlesinger et al. .......... | 514/15 |
| 4,327,072 A | * | 7/1997 | Inouye et al. .................. | 424/1 |
| 5,643,868 A | * | 7/1997 | Weiner et al. .................. | 514/3 |

FOREIGN PATENT DOCUMENTS

| | | |
|---|---|---|
| CA | 1176158 | 10/1984 |
| EP | 0132769 A1 | 7/1984 |
| EP | 0 171 887 A2 | 6/1988 |
| EP | 0678522 A1 | 2/1990 |
| EP | 0 562 508 A2 | 3/1993 |
| GB | 2104382 B | 12/1984 |
| WO | WO 9312221 | 6/1993 |
| WO | WO 9321223 | 10/1993 |
| WO | WO 9425071 | 11/1994 |
| WO | WO 9506122 | 3/1995 |
| WO | WO 9601846 | 1/1996 |
| WO | WO 96/05309 | 2/1996 |
| WO | WO 9605309 | 2/1996 |
| WO | WO 9614334 | 5/1996 |
| WO | WO 9634885 | 11/1996 |
| WO | WO 9733909 | 9/1997 |
| WO | WO 9802555 | 1/1998 |

OTHER PUBLICATIONS

The Diabetes Cotnrol and Complications Trial Research Group, "The Effect of Intensive Treatment of Diabetes on . . . " The New England Journal of Medicine, vol. 329, No. 14, Sep. 30, 1993, pp. 977–986.

Thomas Kieber–Emmons et al., "Therapeutic peptides and peptidomimetics", Current Opinion in Biotechnology, vol. 8, No. 4, Aug. 1997, pp. 435–441.

Tim Clackson et al., "In vitro selection from protein and peptide libraries", Biotechnology, vol. 12, May 1994, pp. 173–184.

Torben Clausen et al., "Regulation of the Na,K–pump in skeletal muscle", Kidney International, vol. 35, No. 1, 1989, pp. 1–13.

Douglas A. Greene et al., "Impaired Rat Sciatic Nerve Sodium–Potassium Adenosin Triphosphatase in Acute Streptozocin Diabetes . . . ", The Journal of Clinical Investigation, vol. 72, Jul.–Dec. 1983, pp. 1058–1063.

Rolf Geiger et al., "Syntheseplan und Darstellung der Sequenz 28–31 des Human–Proinsulin–C–Peptids", Chemische Berichte, vol. 106, 1973, pp. 188–192.

Y. Ido et al., "Prevention of Vascular and Neural Dysfunction in Diabetic Rats by C–Peptide", Science, vol. 277, Jul. 25, 1997, pp. 445–608.

Leslie C. MacGregor et al., "Experimental Diabetes Mellitus Impairs the Function of the Retinal Pigmented Epithelium", Metabolism Clinical and Experimental, vol. XXXV, No. 4, Suppl 1, Apr. 1986, pp. 28–34.

Keld Kjeldsen et al., "Diabetes Decreases Na–K Pump Concentration in Skeletal Muscles, Heart Ventricular Muscle, and Peripheral Nerves of Rat", Diabetes, vol. 36, Suppl. 1, May 1987, pp. 842–848.

Hiroshi Nakanishi et al., "Peptidomimetics of the immunoglobulin supergene family a reveiw", Gene, vol. 137, No. 1, 1993, pp. 51–56.

Y. Ohtomo et al., "C–peptide stimulates rat renal tubular Na, K –ATPase activity in synergism with neuropeptide Y", Diabetologia, vol. 39, No. 2, Feb. 1996, pp. 199–205.

Rudolf Rigler, " Fluorescence correlations, single molecule detection and large number screening Applications in biotechnology", Journal of Biotechnology, vol. 41, No. 2,3, Jul. 31, 1995, pp. 177–186.

(List continued on next page.)

*Primary Examiner*—Bennett Celsa
(74) *Attorney, Agent, or Firm*—Fish & Richardson PC

(57) ABSTRACT

The invention features peptides that are fragments of the human insulin C-peptide, which peptides include the sequence ELGGGPGAG or a fragment thereof, or the sequence EGSLQ or a fragment thereof. The peptides have the ability to stimulate $Na^+K^+ATPase$ activity. Also provided are biomimetic organic compounds exhibiting activation of $Na^+K^+ATPase$ activity and/or cellular binding to renal tubule cells and fibroblasts. Such peptides and compounds are useful in combating diabetes and diabetic complications, or for stimulating $Na^+K^+ATPase$ activity.

27 Claims, 1 Drawing Sheet

OTHER PUBLICATIONS

B L Johansson et al., "The influence of human c–peptide on renal function and glucose utilization in Type 1 (insulin–dependent) diabetic patients", Diabetologia, 1992, 35: 121–128.

B–L Johansson et al., "Effects of C–peptide on blood flow, capillary diffusion capacity and glucose utilization in the exercising forearm of Type 1 (insulin–dependent) . . . ", Diabetologia, 1992, 35: 1151–1158.

B–L Johansson et al., "Influence of combined C–peptide and insulin administration on renal function and metabolic control in diabetes type 1", J Clin Endocrinol & Metab, 1993, 77: 976–981.

J Wahren et al., "Physiological effects of C–peptide in Type 1 diabetes mellitus. In: Frontiers in Insulin Pharmacology, M Berger and FA Cries, eds.", Georg Thieme Verlag Stuttgart, 1993; pp. 149–160.

J Wahren et al., "Does C–peptide have a physiological role", Diabetologia 1994; 37: Suppl 2, 99–107

W Wu et al., "Effect of C–peptide administration on whole body glucose utilization in STZ–induced diabetic rats", Acta Physiol Scand, 1996; 157: 253–258.

B–L Johansson et al., "C–peptide improves autonomic nerve function in patients with type 1 diabetes", Diabetologia, 1996; 39: 687–695.

Wahren et al., "C–peptide revisited—new physiological effects and therapeutic implications", J Intern Med, 1996; 240: 115–124.

V Leclerqc–Meyer et al., "Effect of C–peptide on insuln and glucagon release by isolated perfused rat pancreas", Diabetes & Metabolism 1997, 23:00–00.

J Wahren et al., "Does C–peptide have a role in the pathophysiology of type 1 diabetes?", In Glucose Fluxes, Exercise and Diabetes, Eds. R. Kawamori, M. Vranic, E.S. Horton, M. Kubota. 1995; pp 201–209; Smith–Gordon, Great Britain.

P Oskarsson et al., "Effects of C–peptide on insulin–induced hypoglycaemia and its counterregulatory responses in IDDM patients", Diabetic Medicine, 14:655–659, 1997.

Philip E. Oyer et al., "Isolation and amino acid sequence of the human pancreatic C–peptide", Studies on Proinsulin, vol. 246, No. 5, Mar. 10, 1971, pp. 1375–1386.

Arthur S.C. Ko et al., "The Amino Acid Sequence of the C–peptide of Human Proinsulin", Eur J. Biochem, vol. 20, No. 2, Feb. 3, 1971, pp. 190–199.

O.K. Faber M.D. et al., "Diabetes 27", Characterization of Seven C–peptide Antisera, Suppl 1, 17, 1978, pp. 170–177.

Noboru Yanaihara et al., "Synthesis of human connecting peptide derivatives and their immunological properties", Biochemical and Biophysical Research Communications, vol. 59, No. 3, 1974, pp. 1124–1130.

Hideshi Kuzuya et al., "Heterogeneity of Circulating C–Peptide", J. Clin Endocrinolonol Metab 44: 952, 1977, pp. 952–962.

V.K. Naithani, "The Synthesis of C–Peptide of Human Proinsulin", Hoppe Seyler's Z. Physiol. Chem., 354, Jun. 1973, pp. 659–672.

Mitsuaki Narita et al., "The Easy Disruption o fhte B–Sheet Structure of Resin–Bound Human Proinsulin C–Peptide Fragments by Strong Electron–Donor Solvents", Bull Chemical Society of Japan, vol. 62, No. 11, 1989, pp. 3582–3586.

Ching–I Niu et al., "Conformational Studies on Human Proinsulin Fragments: The Pentapeptide Derivative Bpoc–Gly–Pro–Gly–Ala–Gly–OH and Its Synthetic Intermediates", Biopolymers, vol. 25 1986, s157–s167.

Darryl P. Abriola et al., "Active Site of Human Liver Aldehyde Dehydrogenase", Biochemistry, 26, 1987, pp. 5679–5684.

Noboru Yanaihara Ph.D. et al., "Synthesis of C–peptides and Human Proinsulin", Diabetes 27, suppl. 1, 1978, pp. 149–160.

Noboru Yanahara et al., "Synthetic Study on Human C–Peptide and its Related Peptides", Hoppe–Seyler's Z. Physiol. Chem. 362, Jun. 1981, pp. 775–797.

Vinod K. Naithani et al., "Improved Synthesis of Human Proinsulin C–Peptide and its Benzyloxycarbonyl derivative. Circular Dichroism and Immunological Studies of Human C–Peptide", Hoppe–Seyler's Z. Physiol. Chem., 356, Jun. 1975, pp. 997–1010.

Rolf Geiger et al., "Syntheseplan und Darstellung der Sequenz 28–31 des Human–Proinsulin–C–Peptides", Chemische Berichte, 106, 1973, pp. 188–192.

Narita et al., "Design of the synthetic route for peptides and proteins based on the solubility prediction method", Bull Chemical Society of Japan, 59, 1986, 2445.

Narita et al., "Design of the synthetic route for peptides and proteins based on the solubility prediction method", Bull Chemical Society of Japan, 59, 1986, 2439.

Narita et al., "Design of the synthetic route for peptides and proteins based on the solubility prediction method", Bull Chemical Society of Japan, 59, 1986, 2433.

Narita et al., "Infrared spectroscopic conformational analysis of polystyrene resin–bound human proinsulin C–Peptide fragments", Bull Chemical Society Japan, 61, 1988, 1201.

Narita et al., "Peptide segment separation by tertiary peptide bonds", Bull Chemical Society Japan, 62, 1989, 3577.

Niu Ching–I et al., "Solid–phase synthesis of larger peptides by a new strategy of detachment form the resin", Biopolymers, 20, 1981, 1833.

Donald F. Steiner et al, "Proinsulin C–Peptide–Biological Activity?", Science, vol. 277, Jul. 25, 1997, pp. 531–532.

Douglas A. Greene et al., "Impaired Rat Sciatic Nerve Sodium–Potassium Adenosine Triphosphates in Acute Streptozocin Diabetes and its Correction by Dietary Myo–Inositol Supplementation", The American Society for Clinical Investigation, Inc., vol. 72, Sep. 1983, pp. 1058–1063.

Biochemical Basis of Microvascular Disease, Chapter 54, pp. 534–545.

Geiger R. Volk, "Zur Synthese von Peptiden mit Eigenschaften des Human–Proinsulin–C–Peptids (h C–peptid)", Chemische Berichte, 106, 1973, pp. 199–205.

Huang et al., "Acute Effects Of Human C–Peptide On Renal Function In The Early Stage Of Experimental Diabetes" Diabelogia, vol. 37 (Suppl. 1) A187, 1994.

Johansson, B–L et al., "Does C–Peptide Have A Physiological Role And Should It Be Added In The Treatment Of Patients With Type 1 Diabetes?" J. of Pediatric Endocrinol. Metab., vol. 8, No. 3, 1995.

Johansson, B–L. et al., "Effects Of C–Peptide On Nephropathy And Neuropathy In IDDM Patients–A Clinical Study" Diabetes, vol. 44 (Suppl. 1), 1995, p. 334.

Johansson, B–L. et al., "Combined C–Peptide And Insulin Treatment Improved Renal And Nerve Function In IDDM Patients" Diabelogia, vol. 38 (Supp. 1) A6, 1995.

Johansson, B–L. et al., "Influence Of C–Peptide On Incipient Nephrology And Neuropathy In IDDM Patients–A Clinical Study" Thrid European Meeting for the Implementation of the St. Vincent Declaration, Athens, Greece Mar. 29–Apr. 1, 1995.

Johansson, B–L. et al., "Human Biosynthetic C–Peptide Improves Autonomic Nerve Function In Patients With Type 1 Diabetes" European J. of Endicrinology, vol. 130 (Suppl. 1):25, 1994.

Forbes et al., "C–Peptide Improves Nerve Function In Type 1 Diabetic Patents With Autonomic Neuropathy" Diabetologia vol. 38(Suppl. 1):A238, 1995.

Wahren et al., "Effects Of C–Peptide On Autonomic Nerve Dysfunction In Patients With Type 1 Diabetes" Thrid Euorpean Meeting for the Implementation of the St. Vincent Declaration, Athens, Greece Mar. 29–Apr. 1, 1995.

Sato et al., "Effect Of Rat C–Peptide On In Vivo Insulin Action In Diabetic Rats" Diabelogia, vol. 39 (Suppl. 1) A181, 1996.

Wahren et al., "Inhibition By C–Peptide Of Insulin Release From The Isolated Perfused Rat Pancreas" European J. Of Endicrinology, vol. 134 (Suppl. 1):10, 1996.

Wahren et al., "C–Peptide Stimulates β–Cell Na+K+–Atpase Activity: A Negative Feedback Mechanism On Insulin Secretion?" European J. Of Endicrinology, vol. 130 (Suppl.):38, 1994.

Körner et al., "C–Peptide Treatment Normalized Reduced Glomerular Na+K+–Atpase Activity In Streptozotocin Diabetic rats" C–Peptide and Type 1 Diabetes Mellitus Inetnational Symposium At Stockholm, Sweden, Sep. 1994.

Wahren et al., "C–Peptides Stimulates Na+K+–Atpase" Diabelogia, vol. 38 (Suppl. 1) A64, 1995.

Wahren et al., "Fragments Of Rat C–Peptide Stimulate β–Cell Na+K+–Atpase Activity" European J. Of Endicrinology, vol. 136 (Suppl. ):16, 1997.

Wahren et al., "Intact But Not Truncates Des(27–31) Rat C–Peptide Stimulates β–Cell Na+K+–Atpase Activity" Diabelogia, vol. 40 (Suppl. 1) A150, 1997.

Wahren et al., "C–Peptide Fragments Stimulate Renal Tubule β–Cell Na+K+–Atpase Activity" Diabelogia, vol. 40 (Suppl. 1) A150, 1997.

Sato et al., "Physiological Levels Of Rat C–Peptide Improves Glucose Utilization In Diabetic Rats" Diabelogia, vol. 40 (Suppl. 1) A274, 1997.

Hehenberger et al., "C–Peptide Increases Proliferation In Fibroblasts Derived From IDDM Patients" European J. Of Endicrinology, vol. 136 (Suppl. ):6, 1997.

Johansson et al., "Effects Of C–Peptide On Microvascular Function In Exercising Forearm Muscle In Type I Diabetes" Diabelogia, vol. 34 (Suppl. 1) A65, 1992.

Wahren et al., "C–Peptide Augments The Vasoconstrictor Effect Of NPY And Increases Forearm Blood Flow In IDDM Patients" European J. Of Endicrinology, vol. 134 (Suppl. 1):19, 1996.

Forbes et al., "Effects Of C–Peptide On Blood Flow In IDDM Patients: An Endothelium–Mediated Function?" European J. Of Endicrinology, vol. 136 (Suppl. ):16, 1997.

Johansson et al., "C–Peptide Augments The Vasoconstrictor Effect Of NPY And Increases Forearm Blood Flowing IDDM Patients" Diabelogia, vol. 39 (Suppl. 1) A181, 1986.

Johansson et al., "C–Peptide Potentiates The Effect Of Neuropeptide Y On Forearm Blood Flow In IDDM Patients" European J. of Endicrinology, vol. 26 (Suppl. ):A11, 1996.

Johansson et al., "Effects Of C–Peptide On Forearm Blood Flow In IDDM Patients Seen Not To Be Endothelium–Mediated" Diabelogia, vol. 40 (Suppl. 1) A239, 1997.

Johansson et al., "Effects Of C–Peptide On Forearm Blood Flow In IDDM Patients: An Endothelium–Mediated Function?" Second International Congress, Stockholm, Sweden Aug., 1997.

Johansson et al., "Human C–Peptide Stimulates Exercise–Induced Oxygen Uptake In Type 1 Diabetic Patients" Diabelogia, vol. 36 (Suppl. 1) A22, 1993.

Wahren et al., "C–Peptide Augments The Vasoconstrictor Effect Of NPY And Increases Forearm Blood Flow In IDDM Patients" European J. of Endicrinology, vol. 36 (Suppl.):A22, 1993.

Forbes et al., "Effects Of C–Peptide On Blood Flow In IDDM PAtients: An Endothelium–Mediated Function?" European J. of Endicrinology, vol. 136 (Suppl. ):16, 1997.

Steiner et al., "Biosynthesis Of Proinsulin, Insulin and C–peptide" Abstract of a Presentation or Poster from The International Symposium on "C–Peptide And Type 1 Mellitus", Karolinska Institute, Stockholm, Sweden, Sep. 23–24, 1994.

Rubenstein, "Historical Review Of Biological Effects of C–Peptide" Abstract of a Presentation or Poster from The International Symposium on "C–Peptide And Type 1 Mellitus", Karolinska Institute, Stockholm, Sweden, Sep. 23–24, 1994.

Williamson et al. "Effect Of C–Peptide On Vascular Dysfunction In Animal Models Of Diabetes" Abstract of a Presentation or Poster from The International Symposium on "C–Peptide And Type 1 Mellitus", Karolinska Institute, Stockholm, Sweden, Sep. 23–24, 1994.

Johnsson et al. "Acute Effects Of C–Peptide On Microvascular Exchange In Rat Skeletal Muscle And Kidney" Abstract of a Presentation or Poster from The International Symposium on "C–Peptide And Type 1 Mellitus", Karolinska Institute, Stockholm, Sweden, Sep. 23–24, 1994.

Kernell et al. "Blood–Retinal Barrier Function In Type 1 Diabetes And C–Peptide" Abstract of a Presentation or Poster from The International Symposium on "C–Peptide And Type 1 Mellitus", Karolinska Institute, Stockholm, Sweden, Sep. 23–24, 1994.

Sundkvist et al. "Diabetic Neuropathy–An Overview" Abstract of a Presentation or Poster from The International Symposium on "C–Peptide And Type 1 Mellitus", Karolinska Institute, Stockholm, Sweden, Sep. 23–24, 1994.

Ido et al. "Prevention Of Electrophysiological Dysfunction And Decreased NA+K+/Atpase Activity In Peripheral Nerve Of Diabetic Rats By C–Peptide" Abstract of a Presentation or Poster from The International Symposium on "C–Peptide And Type 1 Mellitus", Karolinska Institute, Stockholm, Sweden, Sep. 23–24, 1994.

Borg et al. "Influence Of C–Peptide Infusion On Peripheral Nerve Function In Patients With Diabetic Polyneuropathy" Abstract of a Presentation or Poster from The International Symposium on "C–Peptide And Type 1 Mellitus", Karolinska Institute, Stockholm, Sweden, Sep. 23–24, 1994.

Broberger et al. "C–Peptide Like Immunoreactivity In Neurons In The Rat Brain" Abstract of a Presentation or Poster from The International Symposium on "C–Peptide And Type 1 Mellitus", Karolinska Institute, Stockholm, Sweden, Sep. 23–24, 1994.

Aperia et al. "C–Peptide Stimulates Rat Renal Tubular Na+K+–Atpase Activity In Synergism With Neuropeptide Y" Abstract of a Presentation or Poster from The International Symposium on "C–Peptide And Type 1 Mellitus", Karolinska Institute, Stockholm, Sweden, Sep. 23–24, 1994.

Sahlgren "C–Peptide And Intracellular Ca++ Concentrations In Proximal Tubule Cells" Abstract of a Presentation or Poster from The International Symposium on "C–Peptide And Type 1 Mellitus", Karolinska Institute, Stockholm, Sweden, Sep. 23–24, 1994.

Wojcikowski et al., "Early Studies Of Pharmacological Effects Of C–Peptide" Abstract of a Presentation or Poster from The International Symposium on "C–Peptide And Type 1 Mellitus", Karolinska Institute, Stockholm, Sweden, Sep. 23–24, 1994.

Sato et al. "C–Peptide And Whole Body Glucose Metabolism In Diabetic Rats" Abstract of a Presentation or Poster from The International Symposium on "C–Peptide And Type 1 Mellitus", Karolinska Institute, Stockholm, Sweden, Sep. 23–24, 1994.

Viberti "Diabetic Nephropathy—An Overview" Abstract of a Presentation or Poster from The International Symposium on "C–Peptide And Type 1 Mellitus", Karolinska Institute, Stockholm, Sweden, Sep. 23–24, 1994.

Sjoquist et al. "The Effects Of Human C–Peptide On Renal Function In The Early State Of Experimental Diabetic Rats" Abstract of a Presentation or Poster from The International Symposium on "C–Peptide And Type 1 Mellitus", Karolinska Institute, Stockholm, Sweden, Sep. 23–24, 1994.

Polonsky "C–Peptide Kinetics After Intravenous Administration" Abstract of a Presentation or Poster from The International Symposium on "C–Peptide And Type 1 Mellitus", Karolinska Institute, Stockholm, Sweden, Sep. 23–24, 1994.

Linde "Absorption Of C–Peptide After Subcutaneous Injection In Type 1 Diabetic Patients" Abstract of a Presentation or Poster from The International Symposium on "C–Peptide And Type 1 Mellitus", Karolinska Institute, Stockholm, Sweden, Sep. 23–24, 1994.

Johansson et al. "Influence Of C–Peptide Administration On Urinary Albumin Excretion Autonomic Neuropathy And Blood Retinal Barrier Function In Patients With Type 1 Diabetes—A Clinical Study" Abstract of a Presentation or Poster from The International Symposium on "C–Peptide And Type 1 Mellitus", Karolinska Institute, Stockholm, Sweden, Sep. 23–24, 1994.

Santiago et al. "Biosynthetic Human C–Peptide Treatment In Iddm: Effects On Glomerular And Retinal Function And Fibrinolytic Status" Abstract of a Presentation or Poster from The International Symposium on "C–Peptide And Type 1 Mellitus", Karolinska Institute, Stockholm, Sweden, Sep. 23–24, 1994.

Korner et al. "C–Peptide Treatment Normalizes Reduced Glomerular Na–K–Atpase Activity In Streptozoticin Diabetic Rats" Abstract of a Presentation or Poster from The International Symposium on "C–Peptide And Type 1 Mellitus", Karolinska Institute, Stockholm, Sweden, Sep. 23–24, 1994.

Jorneskog et al. "Skin Microvascular Reactivity In The Toes Of Type 1 Diabetic Patients During Treatment With C–Peptide" Abstract of a Presentation or Poster from The International Symposium on "C–Peptide And Type 1 Mellitus", Karolinska Institute, Stockholm, Sweden, Sep. 23–24, 1994.

Forbes et al. "Metabolic And Pharmacokinetic Response S To Subcutaneous Injection Of Combined C–Peptide And Insulin In Type 1 Diabetes" Abstract of a Presentation or Poster from The International Symposium on "C–Peptide And Type 1 Mellitus", Karolinska Institute, Stockholm, Sweden, Sep. 23–24, 1994.

Dineson et al. "The Specificity Of C–Peptide Immunoassays" Abstract of a Presentation or Poster from The International Symposium on "C–Peptide And Type 1 Mellitus", Karolinska Institute, Stockholm, Sweden, Sep. 23–24, 1994.

Oskarsson et al. "Effect Of Exogenous C–Peptide On the Glucagons Response To Insulin–Induced Hypoglycemia In Patients With IDDM" Abstract of a Presentation or Poster from The International Symposium on "C–Peptide And Type 1 Mellitus", Karolinska Institute, Stockholm, Sweden, Sep. 23–24, 1994.

Hyllienmark et al. "Subclinical Peripheral Nerve Dysfunction In Juvenile Diabetics. Relation To Metabolic Control, Height And Levels Of C–Peptide" Abstract of a Presentation or Poster from The International Symposium on "C–Peptide And Type 1 Mellitus", Karolinska Institute, Stockholm, Sweden, Sep. 23–24, 1994.

* cited by examiner

SEQUENCE LISTING

<160> NUMBER OF SEQ ID NOS: 14

<210> SEQ ID NO 1
<211> LENGTH: 31
<212> TYPE: PRT
<213> ORGANISM: Homo sapiens

<400> SEQUENCE: 1

```
Glu Ala Glu Asp Leu Gln Val Gly Gln Val Glu Leu Gly Gly Gly Pro
 1               5                   10                  15

Gly Ala Gly Ser Leu Gln Pro Leu Ala Leu Glu Gly Ser Leu Gln
            20                  25                  30
```

<210> SEQ ID NO 2

```
<211> LENGTH: 9
<212> TYPE: PRT
<213> ORGANISM: Homo sapiens

<400> SEQUENCE: 2

Glu Leu Gly Gly Gly Pro Gly Ala Gly
  1               5

<210> SEQ ID NO 3
<211> LENGTH: 5
<212> TYPE: PRT
<213> ORGANISM: Homo sapiens

<400> SEQUENCE: 3

Glu Gly Ser Leu Gln
  1               5

<210> SEQ ID NO 4
<211> LENGTH: 4
<212> TYPE: PRT
<213> ORGANISM: Homo sapiens

<400> SEQUENCE: 4

Glu Leu Gly Gly
  1

<210> SEQ ID NO 5
<211> LENGTH: 6
<212> TYPE: PRT
<213> ORGANISM: Homo sapiens

<400> SEQUENCE: 5

Glu Leu Gly Gly Gly Pro
  1               5

<210> SEQ ID NO 6
<211> LENGTH: 5
<212> TYPE: PRT
<213> ORGANISM: Homo sapiens

<400> SEQUENCE: 6

Gly Gly Pro Gly Ala
  1               5

<210> SEQ ID NO 7
<211> LENGTH: 4
<212> TYPE: PRT
<213> ORGANISM: Homo sapiens

<400> SEQUENCE: 7

Gly Ser Leu Gln
  1

<210> SEQ ID NO 8
<211> LENGTH: 7
<212> TYPE: PRT
<213> ORGANISM: Homo sapiens

<400> SEQUENCE: 8

Gly Gly Gly Pro Gly Ala Gly
  1               5

<210> SEQ ID NO 9
<211> LENGTH: 5
<212> TYPE: PRT
```

```
<213> ORGANISM: Homo sapiens

<400> SEQUENCE: 9

Gly Gly Gly Pro Gly
 1               5

<210> SEQ ID NO 10
<211> LENGTH: 4
<212> TYPE: PRT
<213> ORGANISM: Homo sapiens

<400> SEQUENCE: 10

Gly Gly Gly Pro
 1

<210> SEQ ID NO 11
<211> LENGTH: 4
<212> TYPE: PRT
<213> ORGANISM: Homo sapiens

<400> SEQUENCE: 11

Gly Gly Pro Gly
 1

<210> SEQ ID NO 12
<211> LENGTH: 8
<212> TYPE: PRT
<213> ORGANISM: Homo sapiens

<400> SEQUENCE: 12

Leu Ala Leu Glu Gly Ser Leu Gln
 1               5

<210> SEQ ID NO 13
<211> LENGTH: 7
<212> TYPE: PRT
<213> ORGANISM: Homo sapiens

<400> SEQUENCE: 13

Ala Leu Glu Gly Ser Leu Gln
 1               5

<210> SEQ ID NO 14
<211> LENGTH: 6
<212> TYPE: PRT
<213> ORGANISM: Homo sapiens

<400> SEQUENCE: 14

Leu Glu Gly Ser Leu Gln
 1               5
```

INSULIN C-PEPTIDES

CROSS-REFERENCE TO RELATED APPLICATIONS

This application claims priority to Swedish Application Serial No. 9603533-2, filed on Sep. 27, 1996, and PCT International Application No. PCT/GB97/02627, filed on Sep. 26, 1997.

FIELD OF THE INVENTION

The present invention relates to fragments of the insulin C-peptide and their use in the treatment of diabetes and diabetic complications.

BACKGROUND

Patients with insulin-dependent diabetes mellitus (IDDM), generally synonymous with type 1 diabetes, cannot survive without insulin therapy. IDDM is the classical, life-threatening form of diabetes, the treatment of which was revolutionized by the discovery of insulin in 1922. The prevalence of IDDM in Europe, North America and Japan is 0.25–0.4% of the population. There is a seasonal variation in the incidence of IDDM with more patients presenting in the autumn and winter months. The disorder affects a slight excess of males but this difference becomes less marked with increasing age.

The classical symptoms of IDDM in its acute phase are thirst, large urine volumes, fatigue and weight loss. Less frequent and minor symptoms are muscle cramps, skin infections and blurred vision. Nausea and vomiting may occur in advanced stages and denote impending ketoacidosis and coma. The duration of symptoms is short, usually 2–3 weeks or less. The patients present with high concentrations of glucose and ketone bodies in blood and urine while insulin levels are low or undetectable.

The etiology of IDDM is multifactorial but most likely includes a genetic predisposition for autoimmune reactivity together with environmental triggering, possibly via a virus infection, resulting in partial or complete destruction of the pancreatic beta cells. The destruction of beta cells may have been in progress during the 6–12 months preceding the onset of the disorder. In the acute phase of IDDM insulin deficiency is thus the dominating pathophysiological feature.

After starting insulin treatment many patients enjoy good blood glucose control with only small doses of insulin. There is an early phase, the "honeymoon period", which may last a few months to a year and which probably reflects a partial recovery of beta cell function. This is, however, a temporary stage and ultimately, the progressive autoimmune destruction of the beta cells leads to increasing requirements for exogenous insulin.

While the short term effects of hypoinsulinemia in the acute phase of IDDM can be well controlled by insulin administration, the long term natural history of IDDM is darkened by the appearance in many patients of potentially serious complications. These include the specifically diabetic problems of nephropathy, retinopathy and neuropathy. These conditions are often referred to as microvascular complications even though microvascular alterations are not the only cause. Atherosclerotic disease of the large arteries, particularly the coronary arteries and the arteries of the lower extremities, may also occur.

Nephropathy develops in approximately 35% of IDDM patients particularly in male patients and in those with onset of the disease before the age of 15 years. The diabetic nephropathy is characterized by persistent albuminuria secondary to glomerular capillary damage, a progressive reduction of the glomerular filtration rate and eventually, end stage renal failure.

The prevalence of diabetic retinopathy is highest among young-onset IDDM patients and it increases with the duration of the disease. Proliferative retinopathy is generally present in about 25% of the patients after 15 years duration and in over 50% after 20 years. The earliest lesion of diabetic retinopathy is a thickening of the capillary basement membrane, there is then capillary dilatation and leakage and formation of microaneurysms. Subsequently, occlusion of retinal vessels occurs resulting in hypoperfusion of parts of the retina, oedema, bleeding and formation of new vessels as well as progressive loss of vision.

Diabetic neuropathy includes a wide variety of disturbances of somatic and autonomic nervous function. Sensory neuropathy may cause progressive loss of sensation or, alternatively, result in unpleasant sensations, often pain, in the legs or feet. Motor neuropathy is usually accompanied by muscle wasting and weakness. Nerve biopsies generally show axonal degeneration, demyelination and abnormalities of the vasa nervorum. Neurophysiological studies indicate reduced motor and sensory nerve conduction velocities. Autonomic neuropathy afflicts some 40% of the patients with IDDM of more than 15 years duration. It may evolve through defects in thermoregulation, impotence and bladder dysfunction followed by cardiovascular reflex abnormalities. Late manifestations may include generalized sweating disorders, postural hypotension, gastrointestinal problems and reduced awareness of hypoglycemia. The latter symptom has grave clinical implications.

Several theories have been advanced with regard to possible mechanism(s) involved in the pathogenesis of the different diabetic complications (1). Metabolic factors may be of importance and recent studies demonstrate that good metabolic control is accompanied by significantly reduced incidence of complications of all types (2). Nevertheless, after 7–10 years of good metabolic control as many as 15–25% of the patients show signs of beginning nephropathy, 10–25% have symptoms of retinopathy and 15–20% show delayed nerve conduction velocity indicating neuropathy. With longer duration of the disease the incidence of complications increases further.

C-peptide is a part of the proinsulin molecule which, in turn, is a precursor to insulin formed in the beta cells of the pancreas. Human C-peptide is a 31 amino acid peptide having the following sequence: EAEDLQVGQVELGGGP-GAGSLQPLALEGSLQ (SED ID. NO. 1). It has been suggested in EP 132 769 that C-peptide may be given for the treatment of diabetes and in SE 460334 that insulin in combination with C-peptide can be administered in the treatment of diabetes and in the prevention of diabetic complications.

In recent years it has become apparent that type 1 diabetes is accompanied by consistently reduced activity of the enzyme $Na^+K^+$ATPase in several tissues, notably in renal glomeruli, retina, peripheral nerve, heart and skeletal muscle (3, 4, 5). $Na^+K^+$ATPase is an enzyme that is localized to the cell membrane and generates energy for transcellular transport of $Na^+$ and $K^+$ as well as for all co- or countertransported substrates in all mammalian cells. It is thus obvious that the activity of this enzyme is of fundamental importance for normal cell function. Deficient $Na^+K^+$ATPase activity in nervous tissue, glomeruli and retina is likely to be an important contributing factor in the pathogenesis of diabetic neuropathy, nephropathy and retinopathy. Na⁺K⁺ATPase activity is regulated via the Na⁺ concentration and by hormonal action; several hormones stimulate (thyroid hormone, noradrenalin, angiotensin, neuropeptide Y, insulin) or inhibit (dopamine, ANF) the enzyme's activity (6). Despite insulin treatment sufficient to achieve good glycemic control, patients with type 1 diabetes show signs of insufficient Na⁺K⁺ATPase activity on a long term basis.

BRIEF SUMMARY OF THE INVENTION

The present invention is based on the discovery of a group of peptides from the middle portion and the C-terminal part of the C-peptide molecule which are characterized by a remarkable ability to stimulate Na⁺K⁺ATPase activity. These peptides are all small fragments of the C-peptide molecule. C-peptide itself is able to stimulate Na⁺K⁺ATPase via activation of a G-protein, increase in the intracellular $Ca^{2+}$ concentration and activation of protein phosphatase 2B (7). However, the smaller peptides' stimulatory effect on Na⁺K⁺ATPase activity is similar to or greater than that of C-peptide itself. There is both in vitro and in vivo evidence to indicate that upon administration of one of these peptides together with regular insulin treatment, renal function improves, early signs of retinopathy regress and the function of somatic and autonomic nerves improves. Treatment with these specific peptides, optionally in combination with conventional insulin therapy is thus useful in preventing or substantially retarding the development of late diabetic complications. A potential advantage that the small peptides possess over C-peptide is that they may be administered orally instead of by injection as in the case of C-peptide and insulin.

In one aspect, the present invention thus provides a peptide being a fragment of the human insulin C-peptide, said peptide comprising the sequence ELGGGPGAG (SEQ ID NO. 2) (hereinafter "peptide A") or a fragment thereof, or the sequence EGSLQ (SED ID NO. 3) (hereinafter "peptide E"), or a fragment thereof, and having the ability to stimulate Na⁺K⁺ATPase activity.

In a more particular embodiment, the present invention provides a peptide having the sequence ELGGGPGAG (SEQ ID NO. 2) or EGSLQ (SEQ ID NO. 3), or a fragment thereof.

Especially, the invention provides such peptides for use in therapy and more particularly for use in combatting diabetes and diabetic complications.

In another aspect the present invention provides a pharmaceutical composition comprising a peptide of the invention or a fragment thereof as hereinbefore defined together with at least one pharmaceutically acceptable carrier or excipient.

A yet further aspect of the present invention provides the use of a peptide of the invention, or a fragment thereof, as hereinbefore defined, in the manufacture of a medicament for combatting diabetes or diabetic complications.

As used herein the term "combatting" includes both treatment and prophylaxis.

The present invention thus relates to the use of the following peptides which all are fragments of C-peptide: Peptide A (amino acid sequence ELGGGPGAG) (SEQ ID NO. 2) or components thereof, for example Peptide B (ELGG)(SEQ ID NO. 4), Peptide C (ELGGGP) (SEQ ID NO. 5) or Peptide D (GGPGA) (SEQ ID NO. 6). In addition, the invention includes Peptide E (EGSLQ)(SEQ ID NO. 3) and parts thereof, for example Peptide F (GSLQ) (SEQ ID NO. 7). All are intended for the manufacture of a medicament for treating type 1 diabetes.

Fragments of the invention have been proven to stimulate Na⁺K⁺ATPase activity to varying extent. Thus, studies involving renal tubule cells under in vitro conditions indicate that Peptides A–D stimulate Na⁺K⁺ATPase activity to an extent comparable to that for the whole C-peptide molecule. As much as 90% of the effect is achieved within 3 minutes. Moreover, Peptides E and F possess a stimulatory effect on Na⁺K⁺ATPase of renal cells which is comparable to or greater than that for the whole molecule. Combinations of Peptides A–D with Peptides E or F result in a stimulation of the enzyme activity that is greater than that for either peptide alone. For detailed examples of the stimulatory effects of the above peptides, see Example 1, below.

C-peptide exhibits specific binding to the surface of several cell types, notably renal tubule cells and fibroblasts. When fluorescently labelled C-peptide is incubated with cells it binds to the cell surface. The specificity of the binding is illustrated by the fact that preincubation with unmarked C-peptide prevents binding of the fluorescently labelled C-peptide. When preincubation with the fragments of the invention, particularly with either of fragments E or F was made, the fragments were found to prevent binding of the fluorescently marked C-peptide, demonstrating that the fragments bind specifically to the same binding site on the cell surface as C-peptide itself. For a detailed example of the binding of Fragment E see Example 28, below.

As mentioned above, included within the scope of the invention are peptides comprising the sequences of not only peptides A and E, but also their fragments. In the case of the nonapeptide A, such fragments may be 8 to 2 amino acids in length. In the case of the pentapeptide peptide E, such fragments may be 4 to 2 amino acids in length. Exemplary fragments B, C and D (for peptide A) and F (for peptide E) are listed above, but other fragments are also included.

In the case of peptide A certain studies on Na⁺K⁺ATPase activity, studying the ability of the peptide fragments to stimulate the activity of Na⁺K⁺ATPase of rat renal tubule segments, have shown that one or more of the central tri-glycine residues may be important, and preferred peptide fragments, where peptide A is concerned, thus include at least one, and more preferably, at least two, of the central tri-glycine residues. Thus, in addition to peptides B, C and D mentioned above, representative exemplary peptide fragments include GGGPGAG (SEQ ID NO. 8), GGGPG (SEQ ID No. 9), GGGP (SEQ ID NO. 10), GGP and GGPG (SEQ ID NO. 11).

Furthermore, it has been found that peptides containing non-natural D-amino acid isomers may also be active, including for example the dipeptide D-LG or D,L-LG. Thus, included within the scope of the invention are "non-native" isomers of the "native" L-amino acid C-peptide sequences. Insofar as peptide A is concerned, it is believed that the presence of at least one (if D-peptide) or two (if L-peptide) of the central tri-glycine residues may be important in a 9 amino acid or less peptide segment.

In the case of peptide E, exemplary representative fragments include not only the tetrapeptide, peptide F, but also SLQ and LQ. The C-terminal Q residue is believed to be of importance. Likewise, non-native isomers or derivatives of the peptides e.g. peptides including D-amino acids are included within the scope of the invention.

The invention encompasses peptides comprising the sequences of peptides A and E. Thus, also included within the scope of the invention are peptides having N- and/or C-terminal extensions, or flanking sequences, to the sequences of peptides A and C. Such peptides may include additional amino acids which may either be those provided in the corresponding position in the native human insulion C-peptide or other amino acids (excluding of course the possibility of reconstituting the entire insulin C-peptide). The length of such "extended" peptides may vary, but preferably the peptides of the invention are no more than 25 or 20, especially preferably not more than 15 or 10 amino acids in length. Exemplary peptides include octa-, hepta and hexa-peptides including the sequence of peptide E, e.g. LALEGSLQ (SEQ ID NO. 12), ALEGSLQ (SEQ ID NO. 13) and LEGSLQ (SEQ ID NO. 14).

The peptides of the invention can be used for the treatment of diabetes and diabetic complications, most notably type 1 diabetes and its complications. As used herein the term "diabetic complications" thus includes all complications known in the art to be associated with various forms of diabetes. Whilst not wishing to be bound by theory, the utility of the peptides is believed, as explained above, to be linked to their ability to stimulate $Na^+K^+$ATPase activity. A further aspect of the invention thus includes the peptides for use in, and their use in preparing medicaments for use in stimulating $Na^+K^+$ATPase activity in a subject.

$Na^+K^+$ATPase activity may readily be assayed using techniques known in the art and described in the literature and thus the effect of the peptides in stimulating $Na^+K^+$ ATPase activity may readily be determined (for example, see reference 7).

Thus, the peptides can be used for the manufacture of a medicament for stimulation of $Na^+K^+$ATPase activity, for treating type 1 diabetes patients with retinopathy, for treating type 1 diabetes patients with nephropathy, for treating type 1 diabetes patients with neuropathy and for retarding the development of late diabetic complications. The medicament may comprise insulin. The invention also relates to the method for treatment or prevention of the above given indications.

The peptides of the invention may be used singly or in combination and thus a pharmaceutical composition or medicament may be prepared comprising one or more of the peptides. As mentioned above, a synergy has been observed between peptide A or peptides based on or derived from peptide A (the "peptide A group") and peptide E or peptides based on or derived from peptide E (the "peptide E group"). Thus, synergistic combinations of a peptide from the peptide A group, with a peptide from the peptide E group represent a preferred embodiment of the invention.

The peptides may also be used in combination or conjunction with other agents active or effective to treat diabetes and/or its complications. Such other active agents include for exammple insulin. In such "combination" therapies the peptide(s) and second active agent may be administered together in the same composition or separately in separate compositions, simultaneously or sequentially.

A further aspect of the invention thus provides a product containing a peptide of the invention, or a fragment thereof, as hereinbefore defined together with a further active agent effective to combat diabetes or diabetic complications, as a combined preparation for simultaneous, separate or sequential use in combatting diabetes and/or diabetic complications. Preferably such a further active agent is insulin.

In such combined therapies, where insulin is used, it is to be understood that the term "insulin" encompasses all forms, types and derivatives of insulin which may be used for therapy e.g. synthetic, modified, or truncated variants of the active human insulin sequence.

The compositions of the invention may be administered orally or parenterally by the subcutaneous, intramuscular or intravenous route. The compositions of this invention comprise active fragments/peptides of the C-peptide molecule (e.g. Peptides A–F), together with a L pharmaceutically acceptable carrier therefor and optionally, other therapeutic ingredients, for example human insulin. The total amount of active ingredients in the composition varies from 99.99 to 0.01 percent of weight. The carrier must be acceptable in the sense that it is compatible with other components of the composition and is not deleterious to the recipient thereof.

The compositions may be formulated according to techniques and procedures well known in the art and widely described in the literature, and may comprise any of the known carriers, diluents or excipients. Thus, for example, compositions of this invention suitable for parenteral administration conveniently comprise sterile aqueous solutions and/or suspensions of the pharmaceutically active ingredients (e.g. Peptides A–F) preferably made isotonic with the blood of the recipient, generally using sodium chloride, glycerin, glucose, mannitol, sorbitol, and the like. In addition, the compositions may contain any of a number of adjuvants, such as buffers, preservatives, dispersing agents, agents that promote rapid onset of action or prolonged duration of action and the like.

Compositions of this invention suitable for oral administration may, for example, comprise active fragments/ peptides of the C-peptide molecule (e.g. Peptides A–F) in sterile purified stock powder form preferably covered by an envelope or envelopes (enterocapsule) protecting from degradation (decarboxylation or hydrolysis) of the active peptides in the stomach and thereby enabling absorption of these substances from the gingiva or in the small intestine. The envelope(s) may contain any of a number of adjuvants such as buffers, preservative agents, agents that promote prolonged or rapid release giving an optimal bioavailability of the compositions in this invention, and the like.

In addition, the present invention relates to non-peptide compounds showing the same stimulatory effects as displayed by their C-peptide-derived counterparts. Such peptidomimetics or "small-molecules" capable of mimicking the activity of the naturally occurring proteins or peptides are likely to be better suited for e.g. oral delivery due to their increased chemical stability (8,9).

It is now commonplace in the art to replace peptide or protein-based active agents e.g. therapeutic peptides with such peptidomimetics having functionally-equivalent activity. Various molecular libraries and combinatorial chemistry techiques exist and are available to facilitate the identification, selection and/or synthesis of such compounds using standard techniques (10). Such standard techniques may be used to obtain the peptidomimetic compounds according to the present invention, namely peptidomimetic organic compounds which show substantially similar or the same activation of $Na^+K^+$ATPase and/or cellular binding characteristics as the peptides of the invention, e.g. as described herein in the Examples.

A further aspect of the invention thus provides a biomimetic organic compound based on the peptides of the invention, characterised in that said compound exhibits activation of $Na^+K^+$ATPase and/or cellular binding characteristics to renal tubule cells and fibroblasts at at least the level exhibited by the peptides and peptide fragments of the invention as hereinbefore defined.

DESCRIPTION OF THE DRAWING

The invention will now be described in more detail in the following non-limiting Examples which show, inter L alia, the stimulatory effect of specific peptides on Na+K+ATPase activity, and cell-binding with reference to the drawing in which.

DETAILED DESCRIPTION OF THE INVENTION

EXAMPLE 1

Figure 1:
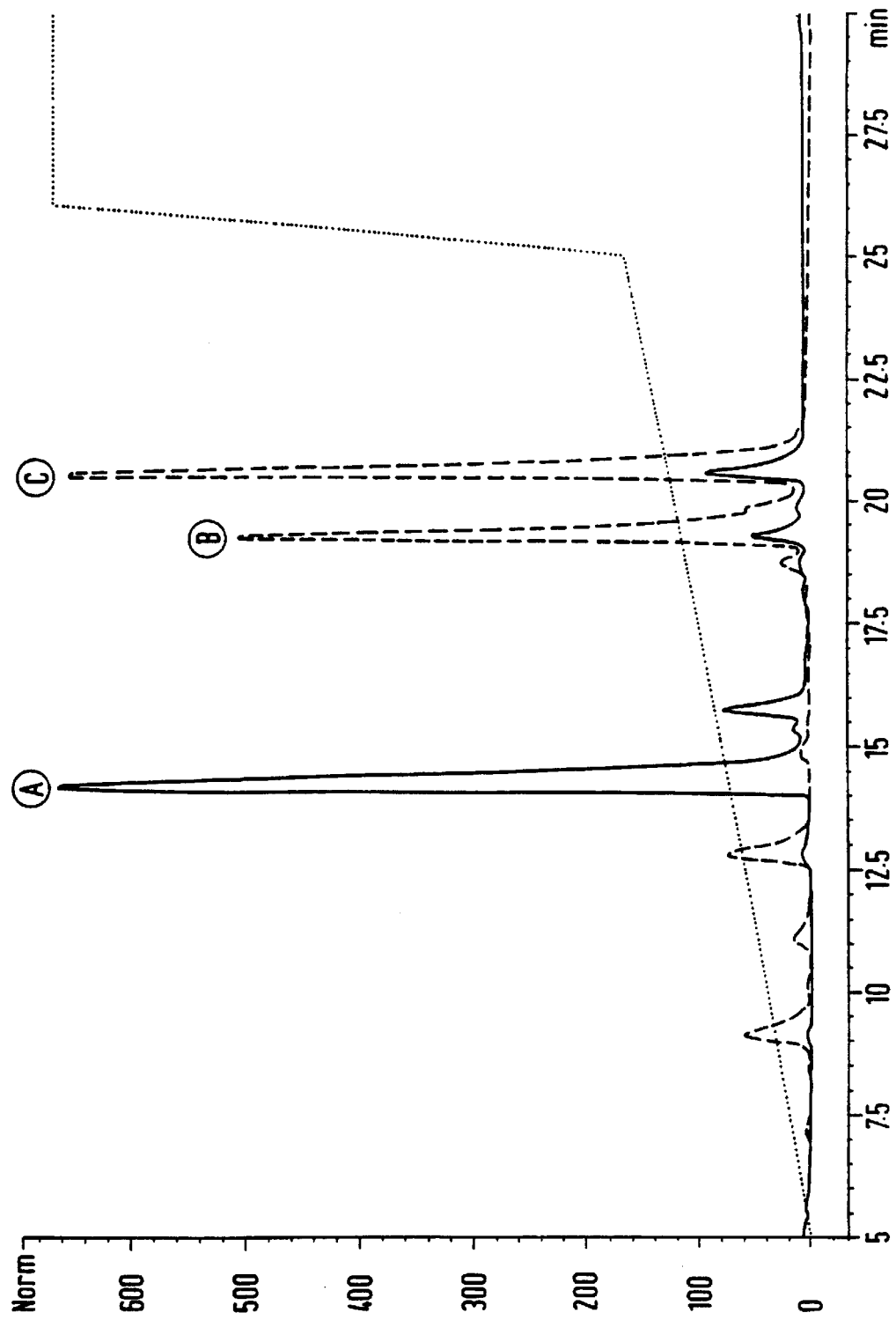
FIG. 1 shows a chromatogram from a preparative reverse phase purification of human C-peptide labelled with tetramethylrhodamine. The column was eluted with a 20 to 40% acetonitrile gradient (acetonitrile in 0.1% trifluoroacetic acid (TFA) during 20 minutes. Peak A corresponds to unreacted fraction of C-peptide. Peaks B and C correspond to C-peptide labelled with tetramethyl-rhodamine. The separation of the B and C peaks corresponds to the presence of two tetramethylrhodamie isomers in the activated reagent. For further studies material from the C-peak was used. Solid line corresponds to absorbtivity at 220 nm (peptide) and dashed line to absorbtivity at 555 nm (tetramethylrhodamine).

The stimulatory effect of Peptides A–F on Na+K+ATPase activity of rat renal tubule cells was examined. Single proximal convoluted tubules were prepared from rat kidneys by micro-dissection. The tubules were incubated for 30 minutes at room temperature with either of Peptides A–F or rat C-peptide 1. Na+K+ATPase activity was then measured following exposure of the tubules to hypotonic shock and incubation for 15 minutes in a medium containing $^{32}$P-ATP in the presence or absence of oubain.

The stimulatory activity of $5$–$10^{-7}$ M rat C-peptide 1 was set at 100%. For the same concentration of Peptides A–F the following relative activities were obtained:

Peptide A 88±3 percent

Peptide B 36±2 percent

Peptide C 46±3 percent

Peptide D 65±4 percent

Peptide E 110±3 percent

Peptide F 96±2 percent

Peptides B+C 86±3 percent

Examples of particular pharmaceutical compositions of this invention are provided in the examples below.

EXAMPLE 2

Human Insulin: Peptide A alone or in equimolar mixture with Peptides B, C, D, E and F (1:4 on a molar basis at 100 Units M insulin per ml).

To prepare 10 ml of the composition, mix

Human Insulin (28 U/mg)—1000 U

Peptide A alone—16.8 mg

M-Kresol—25 mg

Glycerol—160 mg

Water and either 10% hydrochloric acid or 10% sodium hydroxide sufficient to make a composition vloume of 10 ml and a final pH of 7.0–7.8 or a combination with Peptide A—16.8 mg Peptide B—8.8 mg Peptide C—13.6 mg Peptide D—10 mg Peptide E—12.4 mg Peptide F—9.2 mg M-Kresol—25 mg Glycerol—160 mg Water and either 10%—hydrochloride acid or 10% sodium hydroxide sufficient to make a composition volume of 10 ml and a final pH of 7.0–7.8

EXAMPLE 3

Human Insulin: Peptide B (1:4 on a molar basis at 100 Units (U) insulin per ml).

To prepare 10 ml of the composition, mix

Human Insulin (28 U/mg)—1000 U

Peptide B—8.8 mg

M-Kresol—25 mg

Glycerol—160 mg

Water and either 10% hydrochloride acid or 10% sodium hydroxide sufficient to make a composition volume of 10 ml and a final pH of 7.7–7.8

EXAMPLE 4

Human Insulin: Peptide C (1:4 on a molar basis at 100 Units (U) insulin per ml).

To prepare 10 ml of the composition, mix

Human Insulin (28 U/mg)—1000 U

Peptide C—13.6 mg

M-Kresol—25 mg

Glycerol—160 mg

Water and either 10% hydrochloride acid or 10% sodium hydroxide sufficient to make a composition volume of 10 ml and a final pH of 7.0–7.8

EXAMPLE 5

Human Insulin: Peptides D (1:5 on a molar basis at 100 Units (U) insulin per ml).

To prepare 10 ml of the composition, mix

Human Insulin (28 U/mg)—1000 U

Peptide D—10.0 mg

M-kreosol—25 mg

Glycerol—160 mg

Water and either 10% hydrochloride acid or 10% sodium hydroxide sufficient to make a composition volume of 10 ml and a final pH of 7.0–7.8

EXAMPLE 6

Human Insulin: Peptide E (1:4 on a molar basis at 100 Units (U) insulin per ml).

To prepare 10 ml of the composition, mix

Human Insulin (28 U/mg)—1000 U

Peptide E—12.4 mg

M-Kresol—25 mg

Glycerol—160 mg

Water and either 10% hydrochloride acid or 10% sodium hydroxide sufficient to make a composition volume of 10 ml and a final pH of 7.0–7.8

EXAMPLE 7

Human Insulin: Peptide E (1:4 on a molar basis at 100 Units (U) insulin per ml).

To prepare 10 ml of the composition, mix

Human insulin (28 U/mg)—1000 U

Peptides F—9.2 mg

M-Kreosol—25 ml

Glycerol—160 mg

Water and either 10% hydrochloric acid or 10% sodium hydroxide sufficient to make a composition volume of 10 ml and a final pH of 7.0–7.8

EXAMPLE 8

Human Insulin: Peptide A alone or mixed equimolar together with fragments B, C, D, E and F (1:1 on a molar basis at 100 Units (U) insulin per ml).

To prepare 10 ml of the composition, mix

Human Insulin (28 U/mg)—1000 U

Peptide A—4.2 mg

M-Kreosol—25 mg

Glycerol—160 mg

Water and either 10% hydrochloric acid or 10% sodium hydroxide sufficient to make a composition volume of 10 ml and a final pH of 7.0–7.8 or a combination with Peptide A—4.2 mg Peptide B—2.2 mg Peptide C—3.4 mg Peptide D—2.5 mg Peptide E—3.1 mg Peptide F—2.3 mg M-Kreosol—25 mg Glycerol—160 mg Water and either 10% hydrochloric acid or 10% sodium hydroxide sufficient to make a composition volume of 10 ml and a final pH of 7.0–7.8

EXAMPLE 9

Human Insulin: Peptide B (1:1 on a molar basis at 100 Units (U) insulin per ml).

To prepare 10 ml of the composition, mix

Human Insulin (28 U/mg)—1000 U

Peptide B —2.2 mg

M-Kreosol—25 mg

Glycerol—160 mg

Water and either 10% hydrochloric acid or 10% sodium hydroxide sufficient to make a composition volume of 10 ml and a final pH of 7.0–7.8

EXAMPLE 10

Human Insulin: Peptide C (1:1 on a molar basis at 100 Units (U) insulin per ml).

To prepare 10 ml of the composition, mix

Human Insulin (28 U/mg)—1000 U

Peptide C—3.4 mg

M-Kieosol—25 ml

Glycerol—160 mg

Water and either 10% hydrochloric acid or 10% sodium hydroxide sufficient to make a composition volume of 10 ml and a final pH of 7.0–7.8

EXAMPLE 11

Human Insulin: Peptide D (1:1 on a molar basis at 1000 Units (U) insulin per ml).

To prepare 10 ml of the composition, mix

Human Insulin (28 U/mg)—1000 U

Peptide D—2.5 mg

M-Kreosol—25 mg

Glycerol—160 mg

Water and either 10% hydrochloric acid of 10% sodium hydroxide sufficient to make a composition volume of 10 ml and a final pH of 7.0–7.8

EXAMPLE 12

Human Insulin: Peptide E (1:1 on a molar basis at 100 Units (U) insulin per ml).

To prepare 10 ml of the composition, mix

Human Insulin (28 U/mg)—1000 U

Peptide E—3.1 mg

M-Kreosol—25 mg

Glycerol—160 ml

Water and either 10% hydrochloric acid of 10% sodium hydroxide sufficient to make a composition volume of 10 ml and a final pH of 7.0–7.8

EXAMPLE 13

Human Insulin: Peptide E (1:1 on a molar basis at 100 Units (U) insulin per ml).

To prepare 10 ml of the composition, mix

Human Insulin (28 U/mg)—1000 U

Peptide F—2.3 mg

M-Kreosol—25 mg

Glycerol—160 mg

Water and either 10% hydrochloric acid or 10% sodium hydroxide sufficient to make a composition volume of 10 ml and a final pH of 7.0–7.8

EXAMPLE 14

Human Zinc Insulin: Peptide A alone or mixed equimolar together with fragments B, C, D, E and F (1:4 on a molar basis at 100 Units (U) insulin per ml).

To prepare 10 ml of the composition, mix

Human Insulin in modific amorph 300 U and modific cryst

700 U (28 U/mg)—1000 U

Peptide A—16.8 mg

Zinc—1.3 mg

Sodium chloride—70 mg

Sodium Acetate—16 mg

Methyl Parahydroxybenz—10 mg

Water and either 10% hydrochloric acid or 10% sodium hydroxide sufficient to make a composition volume of 10 ml and a final pH of 7.1–7.4 or a combination with Peptide A—16.8 mg Peptide B—8.8 mg Peptide C—13.6 mg Peptide D—10 mg Peptide E—12.4 mg Peptide F—9.2 mg Zinc—1.3 mg Sodium chloride—70 mg Sodium Acetate—16 mg Methyl Parahydroxybenz—10 mg Water and either 10% hydrochloric sodium hydroxide sufficient to make a composition volume and a final pH of 7.1–7.4

EXAMPLE 15

Human Zinc Insulin: Peptide B (1:4 on a molar basis at 100 Units (U) insulin per ml).

To prepare 10 ml of the composition, mix

Human Insulin in modific amorph 300 U and modific cryst 700 U (28 U/mg)—1000 U

Peptide B—8.8 mg

Zinc—1.3 mg

Sodium chloride—70 mg

Sodium Acetate—16 mg

Methyl Parahydroxybenz—10 mg

Water and either 10% hydrochloric acid or 10% sodium hydroxide suficient to make a composition volume of 10 ml and a final pH of 7.1–7.4

EXAMPLE 16

Human Zinc Insulin: Peptide C (1:4 on a molar basis at 100 Units (U) insulin per ml).

To prepare 10 ml of the composition, mix

Human Insulin in modific amorph 300 U and modific cryst 700 U (28 U/mg)—1000 U

Peptide C—13.6 mg

Zinc—1.3 mg

Sodium chloride—70 mg

Sodium Acetate—16 mg

Methyl Parahydroxybenz—10 mg

Water and either 10% hyrochloric acid or 10% sodium hydroxide sufficient to make a composition volume of 10 ml and a final pH of 7.1–7.4

EXAMPLE 17

Human Zinc Insulin: Peptide D (1:4 on a molar basis at 100 Units (U) insulin per ml).

To prepare 10 ml of the composition, mix

Human Insulin in modific amorph 300 U and modific cryst 700 U (28 U/mg)—1000 U

Peptide D—10.0 mg

Zinc—1.3 mg

Sodium chloride—70 mg

Sodium Acetate—16 mg

Methyl Parahydroxybenz—10 mg

Water and either 10% hydrochloric acid of 10% sodium hydroxide sufficient to make a composition volume of 10 ml and a final pH of 7.1–7.4

EXAMPLE 18

Human Zinc Insulin: Peptide E (1:4 on a molar basis at 100 Units (U) insulin per ml).

To prepare 10 ml of the composition, mix

Human Insulin in modific amorph 300 and modific cryst 700 U (28 U/mg)—1000 U

Peptide E—12.4 mg

Zinc—1.3 mg

Sodium chloride—70 mg

Sodium Acetate—16 mg

Methyl Parahydroxybenz—10 mg

Water and either 10% hydrochloric acid of 10% sodium hydroxide sufficient to make a composition volume of 10 ml and a final pH of 7.1–7.4

EXAMPLE 19

Human Zinc Insulin: Peptide F (1:4 on a molar basis at 100 Units (U) insulin per ml).

To prepare 10 ml of the composition, mix

Human Insulin in modific amorph 300 U and modific cryst 700 U (28 U/mg)—1000 U

Peptide F—9.2 mg

Zinc—1.3 mg

Sodium chloride—70 mg

Sodium Acetate—16 mg

Methyl Parahydroxybenz—10 mg

Water and either 10% hydrochloric acid of 10% sodium hydroxide sufficient to make a composition volume of 10 ml and a final pH of 7.1–7.4

EXAMPLE 20

Human Zinc insulin: Peptide A alone or mixed equimolar together with fragments B, C, D, E and F (1:1 on a molar basis at 100 Units (U) insulin per ml).

To prepare 10 ml of the composition, mix

Human Insulin in modific amorph 300 U and modific cryst 700 U (28 U/mg)—1000 U

Peptide A—4.2 mg

Zinc—1.3 mg

Sodium chloride—70 mg

Sodium Acetate—16 mg

Methyl Parahydroxybenz—10 mg

Water and either 10% hydrochloric acid or 10% sodium hydroxide sufficient to make a composition volume of 10 ml and a final pH of 7.1–7.4 or a combination with Peptide A—4.2 mg Peptide B—2.2 mg Peptide C—3.4 mg Peptide D—2.5 mg Peptide E—3.1 mg Peptide F—2.3 mg Zinc—1.3 mg Sodium chloride—70 mg Sodium Acetate—16 mg Methyl Parahydroxybenz—10 mg Water and either 10% hydrochloric acid of 10% sodium hudroxide suffient to make a composition volume of 10 ml and a final pH of 7.1–7.4

EXAMPLE 21

Human Zinc Insulin: Peptide B (1:1 on a molar basis at 100 Units (U) insulin per ml).

To prepare 10 ml of the composition, mix Human Insulin in modific amorph 300 U and modific cryst 700 U (28 U/mg)—1000 U Peptide B—2.2 mg Zinc—1.3 mg Sodium chloride—70 mg
Sodium Acetate—16 mg
Methyl Parahydroxybenz—10 mg
Water and either 10% hydrochloric acid of 10% sodium hydroxide sufficient to make a composition volume of 10 ml and a final pH of 7.1–7.4

EXAMPLE 22

Human Zinc Insulin: Peptide C (1:1 on a molar basis at 100 Units (U) insulin per ml).
To prepare 10 ml of the composition, mix
Human Insulin in modific amorph 300U and modific cryst 700 U
(28 U/mg)—1000 U
Peptide C—3.4 mg
Zinc—1.3 mg
Sodium chloride—70 mg
Sodium Acetate—16 mg
Methyl Parahydroxybenz—10 mg
Water and either 10% hydrochloric acid or 10% sodium hydroxide sufficient to make a composition volume of 10 ml and a final pH of 7.1–7.4

EXAMPLE 23

Human Zinc Insulin: Peptide D (1:1 on a molar basis at 100 Units (U) insulin per ml).
Human Insulin in modific amorph 300 U and modific cryst 700 U
(28 U/mg)—1000 U
Peptide D—2.5 mg
Zinc—1.3 mg
Sodium chloride—70 mg
Sodium Acetate—16 mg
Methyl Parahydroxybenz—10 mg
Water and either 10% hydrochloric acid or 10% sodium hydroxide sufficient to make a composition volume of 10 ml and a final pH of 7.1–7.4

EXAMPLE 24

Human Zinc Insulin: Peptide E (1:1 on a molar basis at 100 Units (U) insulin per ml).
To prepare 10 ml of the composition, mix
Human Insulin in modific amorph 300 U and modific cryst 700 U
(28 U/mg)—1000 U
Peptide E—3.1 mg
Zinc—1.3 mg
Sodium chloride—70 mg
Sodium Acetate—16 mg
Methyl Parahydroxybenz—10 mg
Water and either 10% hydrochloric acid or 10 sodium hydroxide sufficient to make a composition volume of 10 ml and a final pH of 7.1–7.4

EXAMPLE 25

Human Zinc Insulin: Peptide F (1:1 on a molar basis at 100 Units (U) insulin per ml).
To prepare 10 ml of the composition, mix
Human Insulin in modific amorph 300 U and modific cryst 700 U
(20 U/mg)—1000 U
Human Insulin in modific amorph 300 U and modific cryst 700 U
(28 U/mg)—1000 U
Peptide F—2.3 mg
Zinc—1.3 mg
Sodium chloride—70 mg
Sodium Acetate—16 mg
Methyl Parahydroxybenz—10 mg
Water and either 10% hydrochloric acid of 10% sodium hydroxide sufficient to make a composition volume of 10 ml and a final pH of 7.1–7.4

EXAMPLE 26

Peptide A
To prepare sublingual tablets of enterocapsules each containing the composition equimolar to 100 U of insulin, mix
Peptide A—0.42 mg
Lactos—30 mg
et const q s
or in combination of Peptide A: Peptide B: Peptide C: Peptide D: Peptide E: Peptide F: (1:1:1:1:1:1 on molar basis)
To prepare sublingual tablets of enterocapsulas each containing the composition equimolar to 100 U of insulin, mix
Peptide A—0.42 mg
Peptide B—0.22 mg
Peptide C—0.34 mg
Peptide D—0.25 mg
Peptide E—0.31 mg
Peptide F—0.23 mg
Lactos—30 mg
et const q s

EXAMPLE 27

Peptide A
To prepare sublingual tablets or enterocaplulas each containing the composition equimolar to 400 U of insulin, mix
Peptide A—1.67 mg
Lactos—30 mg
et const q s
or in combination of Peptide A: Peptide B: Peptide C: Peptide D: Peptide E: Peptide F (1:1:1:1:1:1 on molar basis)
To prepare sublingual tablets or enterocapsulas each containing the composition equimolar to 400 U of insulin, mix
Peptide A—1.68 mg
Peptide B—0.88 mg
Peptide C—1.36 mg
Peptide D—1.0 mg
Peptide E—1.24 mg
Peptide F—0.92 mg
Lactos—30 mg
et const q s

EXAMPLE 28

The specific binding of Peptide E to the cell surface is illustrated as follows. Human biosynthetic C-peptide (Eli-Lilly, Inc., Indianapolis, USA) was labelled with tetramethylrhodamine using the activated reagent tetramethylrhodamine succinimidyl ester (FluoReporter® Protein labelling kit, Art. no. F-6163; Molecular Probes Europe BV, Leiden, Netherlands). The coupling reaction was performed at pH 8.3 (0.1 M $NaHCO_3$ buffer) with a five-fold stoichiometrical excess of activated reagent to C-peptide. The tetramethylrhodamine group has absorption/emission maxima at 555/580 nm, respectively and is incorporated in the N-terminus of the C-peptide. Labelled C-peptides were purified by gel filtration (desalting against 50 mM phosphate buffer, 0.1 M NaCl, pH 7.4) on a NAP-5 column; Pharmacia Biotech Uppsala, Sweden) and subsequently by preparative reverse phase chromatography (250 mm Kromasil C8 column, diam. 4.6 mm, 7 μm particle size, 10 nm pore size, Eka-Nobel, Surte, Sweden) using a 1090 Hewlett Packard HPLC chromatography system (Grenoble, France) (FIG. 1). Eluted material was immediately adjusted to pH 8 by addition of ammonia and subsequently lyophilized.

Cultured human renal tubule cells (proximal convoluted tubules, PCT) were incubated with the rhodamine labelled C-peptide synthesized as described above. The cells were prepared from the healthy part of a human kidney removed surgically because of hypernephroma. The outer 150 μm of the renal cortex was removed in a microtome and incubated in a collagenase solution (0.05%) at 37° C. for 15 minutes. A tissue suspension was centrifuged and rinsed twice with 0.01% soybean trypsin inhibitor-solution (Gibco Laboratories, Grand Island, N.Y., USA) and a concentrate of PCT fragments and PCT cells were plated onto glass cover slips. The cells were cultured in Dulbecco's Modified Eagle's Medium [DMEM, 20 mmol/l 4-(2-hydroxyethyl)-1-piperazineethane sulphoric acid (Hepes), 24 mmol/l $NaHCO_3$ 50,000 IU/l penicillin and 50 mg/l streptomycin, pH 7.4] with 10% fetal bovine serum (Gibco) in an incubator at 37° C. with 95% $O_2$, and 5% $CO_2$. After 28 hours in culture the medium was changed to DMEM with 1% fetal bovine serum. The cells were examined approximately 18–36 hours later.

The interaction between C-peptide and the cell surface of the tubule cells was recorded using fluorescence correlation spectroscopy (11). Using a C-peptide concentration of 5 nM 92% of the peptide was found to be bound to the cell surface within 50 minutes. In contrast, when the cells were preincubated with 5 μM of Peptide E, C-peptide binding after 50 minutes was no more than 12%. Likewise, when C-peptide had been bound to the cells for 50 minutes and Peptide E was added afterwards, this resulted in dislocation of a major proportion of the C-peptide from its binding site within 4 hours; only 14% remained bound. Similar conditions obtained for peptide F. The results indicate that the peptides—in similarity to C-peptide—bind to a specific binding site on the cell surface.

REFERENCES

1. Biochemical Basis of Microvascular Disease, C. J. Mullarkey and M. Brownlee, p 534–545, in Textbook of Diabetes, Volume 2, editors J. Pickup and G. Williams. Blackwell, Oxford 1991.

2. The effect of intensive treatment of diabetes on the development and progression of long-term complications in insulin-dependent diabetes mellitus, DCCT group. N Engl J Med 1993; 329: 977–983.

3. K. Kjeldsen, H. Brandgaard, P. Sidenius, J. Stenfatt Larsen and A. Nergaard. Diabetes decreases $Na^+K$ pump concentration in skeletal muscles, heart ventricular muscle, and peripheral nerves of rat. Diabetes 1987; 36: 842–848.

4. L. C. MacGregor and F. M. Matschinsky. Experimental diabetes impairs the function of the retinal pigmented epithelium. Metab Clin Exp 1986; 35: suppl 1, 28–34.

5. D. A. Greene and S. A. Lattimer. Impaired rat sciatic nerve sodium potassium adenosine triphosphatase in acute streptozocin diabetes and its correction by dietary myo-inositol supplementation. J Clin Invest 1983; 72: 1058–1063.

6. T. Clausen and M. E. Everts. Regulation of the Na,K-pump in skeletal muscle. Kidney International 1989; 35: 1–13.

7. Y. Ohtomo, A. Aperia, B. L. Johansson and J, Wahren. C-peptide stimulates renal $Na^+K^+ATPase$ activity in synergism with neuropeptide Y. Diabetologia 1996; 39: 199–205.

8. T. Clackson and J. Wells. In vitro selection from protein and peptide libraries. Trends in Biotechnology 1995, 12: 173–184.

9. H. Nakanishi, S Ramurthy, A. Raktabutr, R. Shen and M. Eahn. Peptidomimetics of the immunoglobulin supergene family—a review. Gene 1993, 137: 51–56.

10. T. Kieber-Emons, R. Murali and M. I. Greene. Therapeutic peptides and peptidomimetics. Current Opinion in Biotechnology 1997, 8: 435–441.

11. R. Rigler. Journal of Biotechnology 1995, 41: 177–186.

What is claimed is:

1. A pharmaceutical composition comprising a peptide that (a) comprises the sequence EGSLQ (SEQ ID NO:3), (b) is up to 15 amino acids in length, and (c) has the ability to stimulate $Na^+K^+$ATPase activity.

2. The pharmaceutical composition of claim 1, wherein the peptide is up to 10 amino acids in length.

3. The pharmaceutical composition of claim 1, further comprising at least one additional active agent effective to treat Type I diabetes or a complication thereof.

4. The pharmaceutical composition of claim 3, wherein the additional active agent is insulin.

5. The pharmaceutical composition of claim 1, wherein the sequence of the peptide consists of EGSLQ (SEQ ID NO: 3).

6. The pharmaceutical composition of claim 1, wherein the sequence of the peptide is selected from the group consisting of: LALEGSLQ (SEQ ID NO:12), ALEGSLQ (SEQ ID NO: 13) and LEGSLQ (SEQ ID NO: 14).

7. The pharmaceutical composition of claim 1, wherein at least one amino acid of the up to ten amino acids N-terminally flanking EGSLQ in the peptide is different from the amino acid in the corresponding position in native human insulin C-peptide.

8. The pharmaceutical composition of claim 7, wherein the peptide is up to 10 amino acids in length.

9. The pharmaceutical composition of claim 7, further comprising at least one additional active agent effective to treat Type I diabetes complication thereof.

10. The pharmaceutical composition of claim 9, wherein the additional active agent is insulin.

11. A substantially isolated peptide, the sequence of which consists of EGSLQ (SEQ ID NO: 3).

12. A method of treating diabetes or its complications, or stimulating $Na^+K^+ATPase$ activity in a human or non-human subject, comprising (a) identifying a subject in need of treatment for diabetes or its complications, and (b) administering to the subject a pharmaceutical composition comprising the peptide of claim 11, wherein administration of the pharmaceutical composition treats diabetes or its complications, or stimulates $Na^+K^+ATPase$ activity.

13. A method of treating Type I diabetes or its complications, or stimulating $Na^+K^+ATPase$ activity in a human or non-human subject, comprising (a) identifying a subject in need of treatment for Type I diabetes or its complications, and (b) administering the pharmaceutical composition of claim 1 to the subject, wherein administration of the composition treats diabetes or diabetic complications, or stimulates $Na^+K^+ATPase$ activity.

14. The method of claim 13, wherein the peptide is LALEGSLQ (SEQ ID NO: 12).

15. The method of claim 13, wherein the peptide is ALEGSLQ (SEQ ID NO: 13).

16. The method of claim 13, wherein the peptide is LEGSLQ (SEQ ID NO: 14).

17. The method of claim 13, further comprising administering insulin to the subject.

18. The method of claim 13, wherein the pharmaceutical composition is administered orally.

19. A pharmaceutical composition comprising a peptide of up to 15 amino acids in length that is a fragment of the human insulin C-peptide, said peptide comprising the sequence EGSLQ (SEQ ID NO: 3), and having the ability to stimulate $Na^+K^+ATPase$ activity.

20. A method of treating Type I diabetes or its complications, or stimulating $Na^+K^+ATPase$ activity in a human or non-human subject, comprising (a) identifying a subject in need of treatment for Type I diabetes or its complications, and (b) administering the pharmaceutical composition of claim 19 the subject, wherein administration of the composition treats diabetes or diabetic complications, or stimulates $Na^+K^+ATPase$ activity.

21. The method of claim 20, further comprising administering insulin to the subject.

22. The method of claim 20, wherein the pharmaceutical composition is administered orally.

23. The method of claim 20, further comprising administering insulin to the subject.

24. The method of claim 20, wherein the pharmaceutical composition is administered orally.

25. The pharmaceutical composition of claim 19, wherein the peptide is up to 10 amino acids in length.

26. The pharmaceutical composition of claim 19, further comprising at least one additional active agent effective to treat Type I diabetes or a complication thereof.

27. The pharmaceutical composition of claim 26, wherein the additional active agent is insulin.

* * * * *